(12) United States Patent
Lee et al.

(10) Patent No.: US 9,937,302 B2
(45) Date of Patent: Apr. 10, 2018

(54) NEBULIZING DEVICE AND NEBULIZER

(71) Applicant: DELTA ELECTRONICS, INC., Taoyuan (TW)

(72) Inventors: Kuo-Liang Lee, Taoyuan (TW); Chun-Kai Chuang, Taoyuan (TW)

(73) Assignee: Delta Electronics, Inc., Taoyuan (TW)

( * ) Notice: Subject to any disclaimer, the term of this patent is extended or adjusted under 35 U.S.C. 154(b) by 248 days.

(21) Appl. No.: 15/082,248

(22) Filed: Mar. 28, 2016

(65) Prior Publication Data

US 2016/0206835 A1 Jul. 21, 2016

Related U.S. Application Data

(63) Continuation-in-part of application No. 14/144,181, filed on Dec. 30, 2013.

(30) Foreign Application Priority Data

Sep. 13, 2013 (TW) .............................. 102133093 A

(51) Int. Cl.
*A61M 11/00* (2006.01)
*A61M 15/00* (2006.01)
*B05B 17/06* (2006.01)

(52) U.S. Cl.
CPC ...... *A61M 11/005* (2013.01); *A61M 15/0028* (2013.01); *A61M 15/0085* (2013.01); *B05B 17/06* (2013.01); *A61M 2205/123* (2013.01)

(58) Field of Classification Search
CPC ........... A61L 2209/111; A61L 2209/12; A61L 2209/132; A61L 9/03; A61L 9/12; A61L 9/122; A61L 9/14; A61M 11/00; A61M 11/001; A61M 11/005; A61M 11/06; A61M 15/0003; A61M 15/0006; A61M 15/0018; A61M 15/0028; A61M 15/0065; A61M 15/0066; A61M 15/0085; A61M 15/02; A61M 2021/0016; A61M 2021/0027; A61M 2021/0044; A61M 2039/2426; A61M 2039/248; A61M 21/02; A61M 2205/123; A61M 2205/3386;

(Continued)

(56) References Cited

U.S. PATENT DOCUMENTS

| 4,592,349 A | 6/1986 | Bird |
| 7,971,588 B2 | 7/2011 | Fink et al. |

(Continued)

*Primary Examiner* — Annette Dixon
(74) *Attorney, Agent, or Firm* — Muncy, Geissler, Olds & Lowe, P.C.

(57) ABSTRACT

A nebulizing device includes a medicament storage module, a nebulizing unit, and a first waterproof gasket. In the medicament storage module, a coupling part is connected with an outer surface of a tubular sidewall and aligned with an outlet of the tubular sidewall, and includes an extension wall and a first recess where the nebulizing unit is disposed. The first waterproof gasket is disposed within the first recess and located on a side of the nebulizing unit farther from the outlet. In the first waterproof gasket, a first opening is disposed adjacent to the nebulizing unit, a second opening is disposed opposite to the first opening and located on a side of the first opening farther from the nebulizing unit, the size of the second opening is greater than that of the first opening, and the annular wall structure is connected to the first opening and the second opening.

20 Claims, 7 Drawing Sheets

(58) Field of Classification Search
CPC ............ A61M 2205/584; A61M 39/24; B05B
12/081; B05B 15/00; B05B 17/06; B05B
17/0615; B05B 17/0646; B05B 17/0669;
B05B 3/082; B05B 7/0408
USPC ............ 128/200.14, 200.16, 200.17, 200.18,
128/200.19, 200.23, 200.24, 203.12,
128/203.15; 239/338
See application file for complete search history.

(56) References Cited

U.S. PATENT DOCUMENTS

| | | |
|---|---|---|
| 2006/0207591 A1 | 9/2006 | Gallem et al. |
| 2007/0267010 A1 | 11/2007 | Fink et al. |
| 2008/0060640 A1 | 3/2008 | Waldner et al. |
| 2010/0219263 A1* | 9/2010 | Feriani ................ A61M 11/005 239/102.1 |
| 2013/0119151 A1 | 5/2013 | Moran et al. |

* cited by examiner

NEBULIZING DEVICE AND NEBULIZER

CROSS REFERENCE TO RELATED APPLICATIONS

This application is a continuation-in-part patent (CIP) application of U.S. Ser. No. 14/144,181, filed on Dec. 30, 2013, which claims priority under 35 U.S.C. § 119(a) on Patent Application No(s). 102133093, filed in Taiwan, Republic of China on Sep. 13, 2013, the entire contents of which are hereby incorporated by reference.

BACKGROUND

Technical Field

This invention relates to a nebulizing device and a nebulizer.

Related Art

Recently, various nebulizers, namely sprayers, are widely applied to healthcare or beauty care. The medicated liquid, lotion or essence, etc. is nebulized into smaller vapor molecules by the nebulizing devices so as to easily enter into a human body. For example, they can be applied to health care or treatment of respiratory diseases, or can make skin absorb the medicated liquid or lotion fast or intensify the aroma, etc.

In medical treatment, the nebulizer can transform the liquid medicament into nebulization or nebulized drops and spray them into the mouth of the patient, so that the nebulized drops can be absorbed into the bronchus and lung of the patient for the treatment or remission of the respiratory diseases. The common mesh-type nebulizer utilizes the micropump technology, which uses the collocation of the piezoelectric device and the nozzle plate, as the nebulization mechanism, so that the liquid medicament can be transformed into the nebulized drops and sprayed out.

However, after a long time of usage, some standing water forms at the spraying outlet of the nebulizer, so that the piezoelectric device and the nozzle plate are easily subjected to the electrode oxidization due to the standing water and then become damaged.

SUMMARY

A nebulizing device comprises a medicament storage module, a nebulizing unit and a first waterproof gasket. The medicament storage module includes a bottom wall, a tubular sidewall and a coupling part. The tubular sidewall is connected to the circumference of the bottom wall. The tubular sidewall and the bottom wall form an accommodating recess having an upper opening to accommodate a liquid medicament. The tubular sidewall comprises an outlet, and the bottom wall is extended to the outlet. The coupling part is connected to an outer surface of the tubular sidewall and aligned with the outlet, and includes an extension wall and a first recess. The nebulizing unit is disposed within the first recess to transform the liquid medicament outputted by the outlet into a plurality of nebulized drops and spray them out. The first waterproof gasket is disposed within the first recess and located on a side of the nebulizing unit farther from the outlet, and includes a first opening, a second opening and an annular wall structure. The first opening is disposed adjacent to the nebulizing unit. The second opening is disposed opposite to the first opening and located on a side of the first opening farther from the nebulizing unit. The size of the second opening is greater than that of the first opening. The annular wall structure is connected to the first opening and the second opening.

In one embodiment, the annular wall structure is a concave surface, a flat surface, a jagged surface or a ladder-shaped surface.

In one embodiment, the nebulizing device further comprises a guiding tube detachably coupled with the coupling part of the medicament storage module.

In one embodiment, the extension wall of the coupling part comprises an annular groove disposed on the extension wall and facing an end surface of the guiding tube.

In one embodiment, the nebulizing device further comprises a second waterproof gasket disposed within the annular groove and extended outwards to cover the end surface of the guiding tube.

A nebulizer includes a nebulizing device and a nebulization driving device. The nebulizing device includes a medicament storage module, a nebulizing unit and a first waterproof gasket. The medicament storage module includes a bottom wall, a tubular sidewall and a coupling part. The tubular sidewall is connected to the circumference of the bottom wall. The tubular sidewall and the bottom wall form an accommodating recess having an upper opening to accommodate a liquid medicament. The tubular sidewall comprises an outlet, and the bottom wall is extended to the outlet. The coupling part is connected to an outer surface of the tubular sidewall and aligned with the outlet, and includes an extension wall and a first recess. The nebulizing unit is disposed within the first recess to transform the liquid medicament outputted by the outlet into a plurality of nebulized drops and spray them out. The first waterproof gasket is disposed within the first recess and located on a side of the nebulizing unit farther from the outlet, and includes a first opening, a second opening and an annular wall structure. The first opening is disposed adjacent to the nebulizing unit. The second opening is disposed opposite to the first opening and located on a side of the first opening farther from the nebulizing unit. The size of the second opening is greater than that of the first opening. The annular wall structure is connected to the first opening and the second opening. The nebulization driving device connects to and drives the nebulizing unit to spray the nebulized drops.

In one embodiment, the annular wall structure is a concave surface, a flat surface, a jagged surface or a ladder-shaped surface.

In one embodiment, the nebulizing device further comprises a guiding tube detachably coupled with the coupling part of the medicament storage module.

In one embodiment, the extension wall of the coupling part comprises an annular groove disposed on the extension wall and facing an end surface of the guiding tube.

In one embodiment, the nebulizing device further comprises a second waterproof gasket disposed within the annular groove and extended outwards to cover the end surface of the guiding tube.

Summarily, in the nebulizing device and the nebulizer, the size of the second opening of the first waterproof gasket is greater than that of the first opening, so that the annular wall structure is extended from the first opening toward the second opening to form a non-horizontal surface. Therefore, even if the nebulized drops are condensed into water drops after being sprayed out of the nozzle plate, the water drops will flow to the outside of the second opening instead of becoming standing water at the annular wall structure. Therefore, the nebulizing unit will not soak in the standing water containing the medicament for a long time, and the nebulizing unit may be oxidized or eroded by the medicament as little as possible so the lifespan of the nebulizing unit can be extended.

BRIEF DESCRIPTION OF THE DRAWINGS

The embodiments will become more fully understood from the detailed description and accompanying drawings, which are given for illustration only, and thus are not limitative of the present invention, and wherein.

DETAILED DESCRIPTION OF THE INVENTION

The embodiments of the invention will be apparent from the following detailed description, which proceeds with reference to the accompanying drawings, wherein the same references relate to the same elements.

Figure 1:
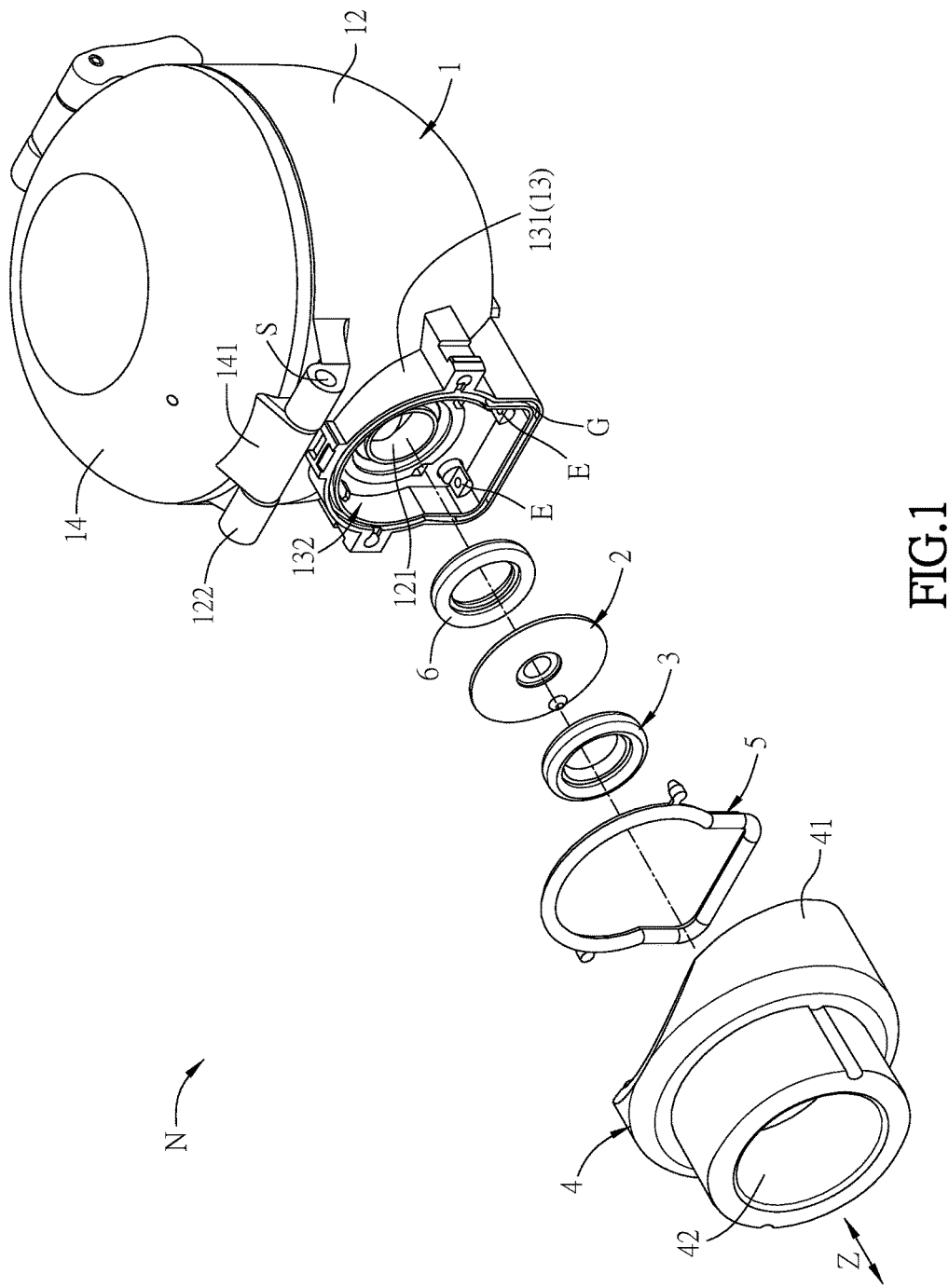
FIG. 1 is a schematic exploded diagram of a nebulizing device of an embodiment of the invention.
Figure 2:
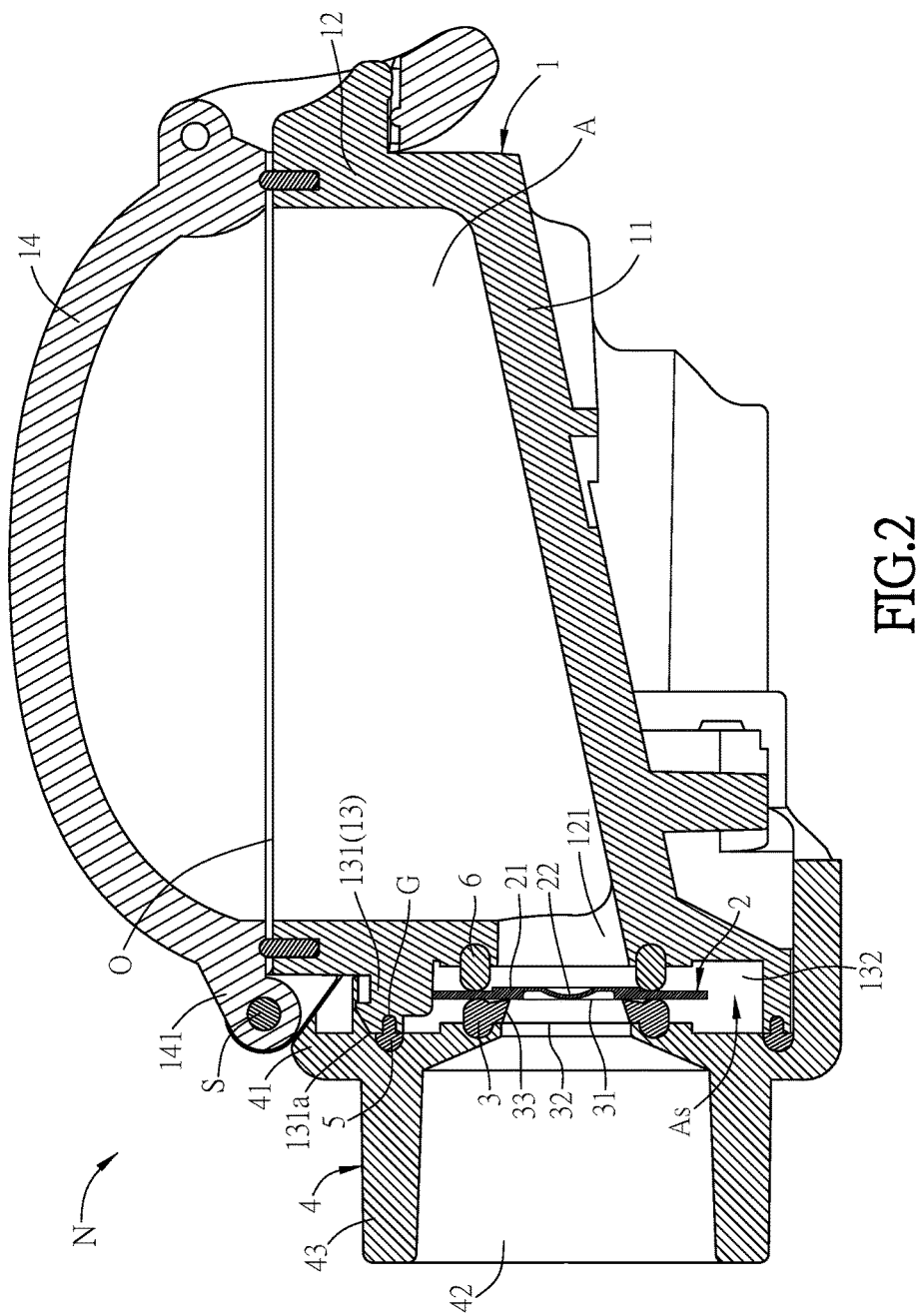
FIG. 2 is a schematic sectional diagram of the nebulizing device of FIG. 1.

FIG. 1 is a schematic exploded diagram of a nebulizing device of an embodiment of the invention, and FIG. 2 is a schematic sectional diagram of the nebulizing device of FIG. 1. As shown in FIGS. 1 and 2, the nebulizing device N of this embodiment is, for example but not limited to, a mesh-type nebulizing device, and can transform or nebulize the liquid (medicament) into a plurality of nebulized drops or aerosol and spray them out, for example, with the size of 1 μm~5 μm. Accordingly, the medicament can be sent to the mouth of the patient and the nebulized drops can be absorbed into the bronchus and lung of the patient for the treatment or remission of the respiratory diseases. Although the nebulizing device N is illustrated as for the medical use for example, the nebulizing device N may also be applied to the beauty use, and this invention is not limited thereto. In this embodiment, the nebulizing device N includes a storage module 1, a nebulizing unit 2 and a first waterproof gasket 3.

Figure 3:
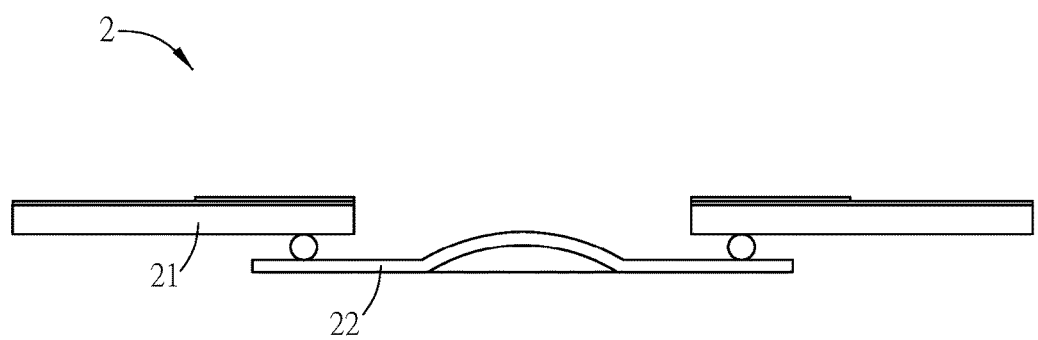
FIG. 3 is a schematic diagram of a nebulizing unit.

FIG. 3 is a schematic diagram of a nebulizing unit. As shown in FIGS. 1 to 3, the nebulizing unit 2 is disposed on the storage module 1 and includes a piezoelectric element 21 and a nozzle plate 22. The piezoelectric element 21 can act as an oscillation element to drive the oscillation of the nozzle plate 22. The nozzle plate 22 includes a plurality of nozzles (not shown). The nozzle plate 22 oscillates in response to the driving of the piezoelectric element 21, and accordingly the liquid medicament can be transformed into very small nebulized drops or aerosol through the above-mentioned nozzles by the micropump principle and then sprayed out. The piezoelectric element 21 can be shaped like an annular sheet and the nozzle plate 22 can be shaped like a disk. The piezoelectric element 21 of this embodiment is disposed around the nozzle plate 22. The first waterproof gasket 3 tightly abuts on the piezoelectric element 21. The nebulizing unit 2 is used to transform the liquid medicament provided by the storage module 1 into a plurality of very small nebulized drops and then spray them out.

As shown in FIGS. 1 and 2, the storage module 1 approximately has a cup structure and includes a bottom wall 11, a tubular sidewall 12 and a coupling part 13. The tubular sidewall 12 favorably has a circular tube shape. The tubular sidewall 12 is connected to the circumference of the bottom wall 11 and can be integrally formed with the bottom wall 11. The tubular sidewall 12 and the bottom wall 11 form an accommodating recess A having an upper opening O to accommodate a liquid medicament. The tubular sidewall 12 has an outlet 121, and that is, the outlet 121 passes through the tubular sidewall 12 to output or supply the liquid medicament. The bottom wall 11 is extended to the outlet 121. The tubular sidewall 12 can be extended vertically along the normal direction of the bottom wall 11 from the circumference of the bottom wall 11. Of course, the bottom wall 11 and the tubular sidewall 12 also can form an included angle therebetween, so that the bottom wall 11 is disposed obliquely, and therefore the liquid medicament can completely flow to the outlet 121 instead of being wasted.

The coupling part 13 is connected to an outer surface of the tubular sidewall 12 and aligned with the outlet 121. In this embodiment, the coupling part 13 is integrally formed with the tubular sidewall 12, and is extended from the outer surface of the tubular sidewall 12 and aligned with the position of the outlet 121. The coupling part 13 includes an extension wall 131 and a first recess 132. The extension wall 131 and the tubular sidewall 12 form the first recess 132. An inner wall surface of the first recess 132 has a multi-step structure for supporting the nebulizing unit 2 so that the nozzle plate 22 of the nebulizing unit 2 can be aligned with the outlet 121. In other words, the nebulizing unit 2 is disposed at the first recess 132 so as to transform the liquid medicament outputted by the outlet 121 into a plurality of nebulized drops or aerosol and spray them out.

Figure 4A:
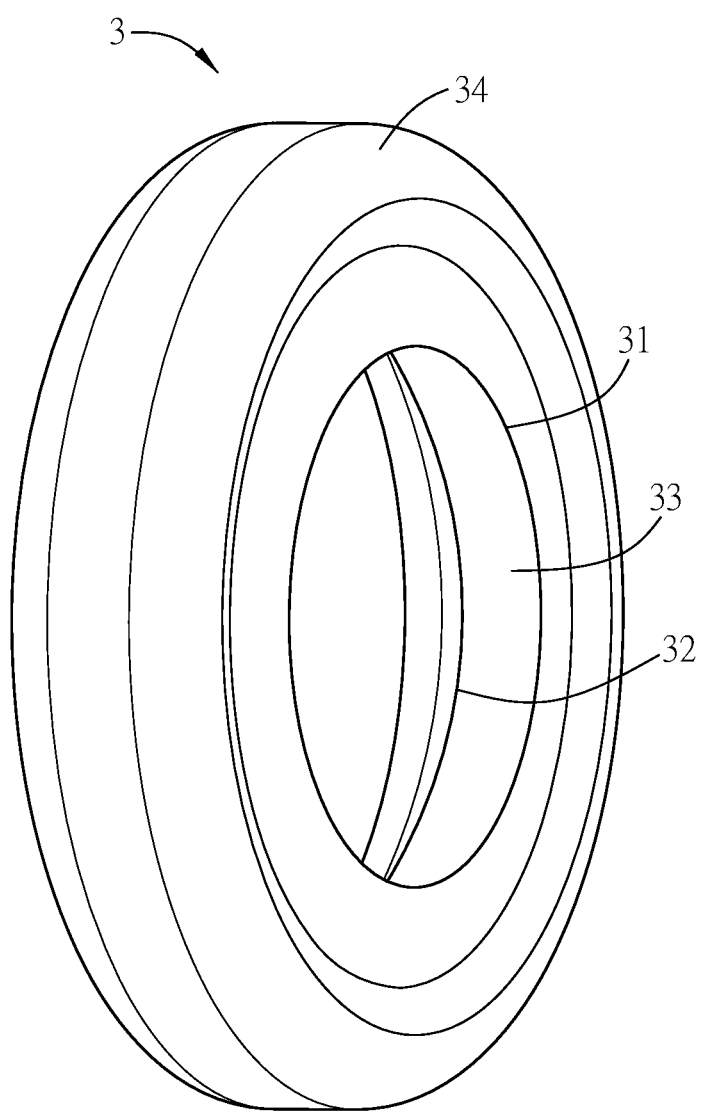
FIG. 4A is a schematic diagram of the first waterproof gasket.
Figure 4B:
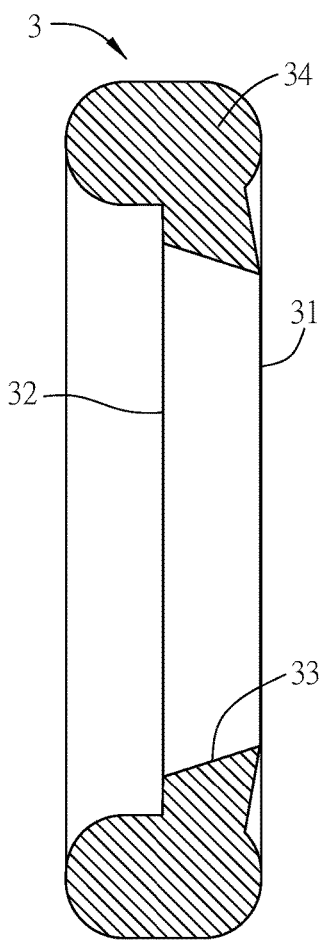
FIG. 4B is a schematic sectional diagram of the first waterproof gasket of FIG. 4A.

Refer to FIGS. 1, 2, 4A and 4B, wherein FIG. 4A is a schematic diagram of the first waterproof gasket and FIG. 4B is a schematic sectional diagram of the first waterproof gasket of FIG. 4A. The first waterproof gasket 3 is disposed in the first recess 132 and on a side of the nebulizing unit 2 farther from the outlet 121. The first waterproof gasket 3 includes a first opening 31, a second opening 32 and an annular wall structure 33. The first opening 31 is disposed adjacent to or abuts upon the nebulizing unit 2 and on a side of the nebulizing unit 2 farther from the outlet 121. The second opening 32 is disposed opposite to the first opening 31 and away from the nebulizing unit 2. That is, the liquid medicament will be sprayed into the mouth of the patient through the outlet 121, the nozzle plate 22, the first opening 31 and the second opening 32 sequentially. The size of the second opening 32 is greater than that of the first opening 31. The annular wall structure 33 is connected to the first opening 31 and the second opening 32. The annular wall structure 33 is extended from the first opening 31 toward the second opening 32 to form a non-horizontal surface. The non-horizontal surface of the annular wall structure 33 may be flat and the section of the annular wall structure 33 shows a straight line from FIG. 4B. Accordingly, because of the size relationship between the second opening 32 and the first opening 31, even if the nebulized drops are condensed into water drops after being sprayed out of the nozzle plate 22, the water drops will continue to flow out of the second opening 32 instead of standing on the non-horizontal surface of the annular wall structure 33. Therefore, the nebulizing unit 2 would not be soaked in the standing water containing the medicament for a long time so at to prevent from being oxidized or eroded by the medicament. Then, the lifespan of the nebulizing unit 2 can be extended.

Figure 4C:
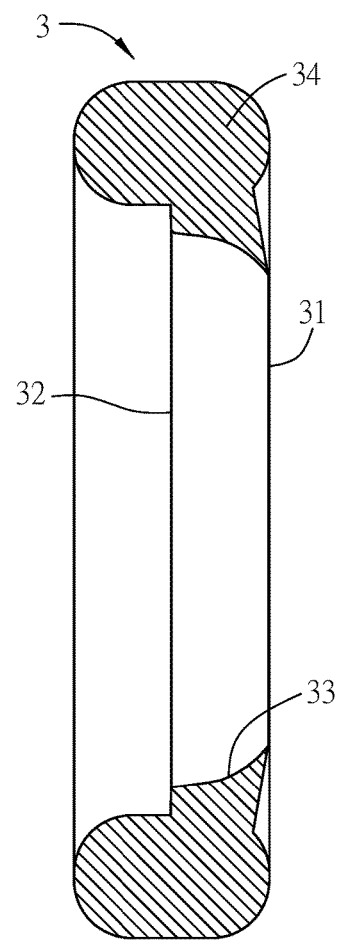
FIGS. 4C to 4E are schematic sectional diagrams of the first waterproof gasket of other embodiments.
Figure 4D:
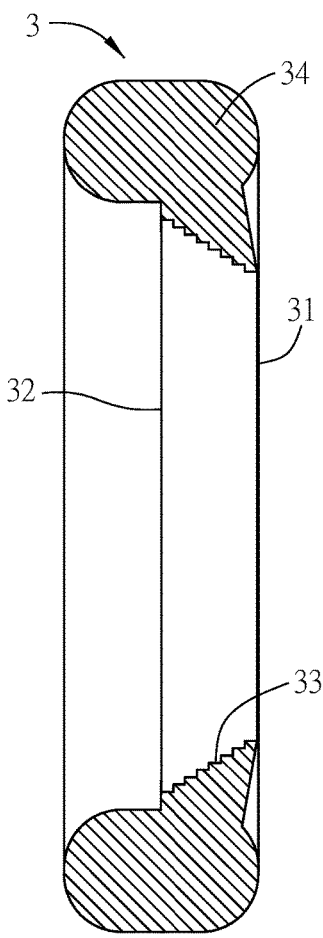
Figure 4E:
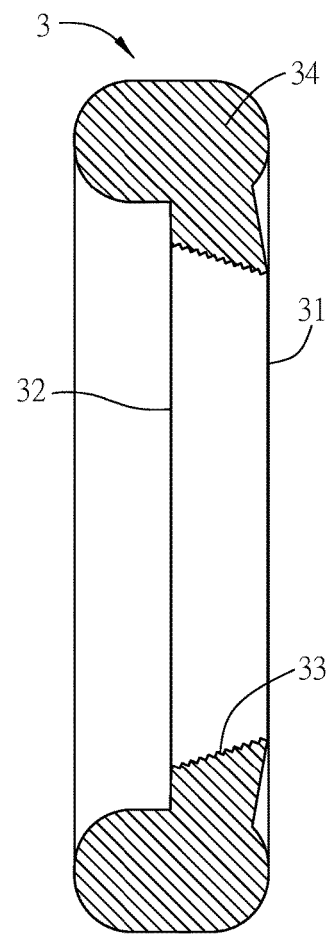

In some embodiments, the non-horizontal surface of the annular wall structure 33 can be a concave surface (as shown in FIG. 4C), a ladder-shaped surface (as shown in FIG. 4D) or a jagged surface (as shown in FIG. 4E), and the above-mentioned effectiveness also can be achieved therefore.

As shown in FIGS. 1 and 2, the nebulizing device N further includes a guiding tube 4 which is detachably coupled with the coupling part 13 of the storage module 1. The guiding tube 4 includes a connection portion 41, an opening 42 and a tube portion 43. The connection portion 41 of the guiding tube 4 is coupled with the extension wall 131 of the coupling part 13, so that the guiding tube 4 is mounted to the coupling part 13. In some embodiments, the extension wall 131 of the coupling part 13 may tightly abut on an inner surface of the connection portion 41. The opening 42 of the guiding tube 4 is correspondingly disposed at or aligned with the nozzle plate 22 of the nebulizing unit 2. The tube portion 43 of the guiding tube 4 guides the plurality of nebulized drops sprayed out by the nebulizing unit 2. The guiding tube 4 can be detachably connected to the storage module 1 and disposed corresponding to the nebulizing unit 2 so as to guide the plurality of nebulized drops sprayed out by the nebulizing unit 2 into the mouth of the patient.

To be noted, an electrode assembly E can be disposed in a region formed within the first recess 132, between the coupling part 13 and the guiding tube 4 and outside the nozzle plate 22 in the radial direction, as shown in FIG. 1 for example. In this embodiment, the electrode assembly includes two electrodes for example. The electrodes E are electrically connected to the piezoelectric element 21 and drive the nozzle plate 22 to oscillate. Therefore, in order to prevent a short circuit of the electrode assembly E, the waterproof structure of this region is also strengthened in this embodiment.

Besides, the first waterproof gasket 3 further includes a coupling ring 34, which is disposed around an outer side of the second opening 32. That is, the diameter of the coupling ring 34 is greater than that of the second opening 32. In this embodiment, the outlet 121, the nozzle plate 22, the first opening 31, the second opening 32, the annular wall structure 33, the coupling ring 34 have a common axis along the axial direction Z. The thickness of the coupling ring 34 along the axial direction Z is greater than the distance between the first opening 31 and the second opening 32. Accordingly, the first waterproof gasket 3 can avoid the leakage of the liquid medicament by the tight abutments of the coupling ring 34 between the nebulizing unit 2 and the guiding tube 4, and also prevent the liquid medicament from permeating into the region where the electrode assembly E is disposed to avoid the short circuit of the electrode assembly E.

Likewise, the nebulizing device N further includes a third waterproof gasket 6, which is disposed between the nebulizing unit 2 and the outlet 121 so as to prevent the liquid medicament from permeating into the region where the electrode E is disposed through the gap between the nebulizing unit 2 and the outlet 121 to avoid the short circuit of the electrode E. The third waterproof gasket 6 and the first waterproof gasket 3 form a hermetic space AS at one end of the first recess 132. The hermetic space AS may be the region where the electrode assembly E is disposed.

The coupling part 13 includes an annular groove G which is disposed on a terminal of the extension wall 131 and faces a sidewall of the connection portion 41 of the guiding tube 4. Additionally, a central axis of the annular groove G is coaxial with that of the extension wall 131. To be noted, the annular groove G can have a circular shape or other ring-like shapes. In this embodiment, the nebulizing device N further includes a second waterproof gasket 5 which is partially disposed within the annular groove G and extended outwards to partially cover the sidewall of the connection portion 41 of the guiding tube 4. Moreover, the second waterproof gasket 5 is also extended along a sidewall 131*a* of the terminal of the extension wall 131 and. That is, the section of the second waterproof gasket 5 can have a mushroom shape as shown in FIG. 2. Therefore, by the disposition of the second waterproof gasket 5, the external liquid (coming from the washing for example) can be prevented from permeating into the region where the electrode E is located through the gap between the guiding tube 4 and the coupling part 13 to avoid the short circuit of the electrode assembly E.

The storage module 1 further includes an upper cover 14, which can be pivotally connected to the tubular sidewall 12 to seal the upper opening O of the accommodating recess A. The tubular sidewall 12 further includes a first pivotal portion 122, and the upper cover 14 includes at least a second pivotal portion 141. The storage module 1 further includes a shaft S passing through the first pivotal portion 122 and the second pivotal portion 141, so that the upper cover 14 can be pivotally connected to the tubular sidewall 12. In some embodiments, the first pivotal portion 122 and the tubular sidewall 12 are integrally formed.

Figure 5:
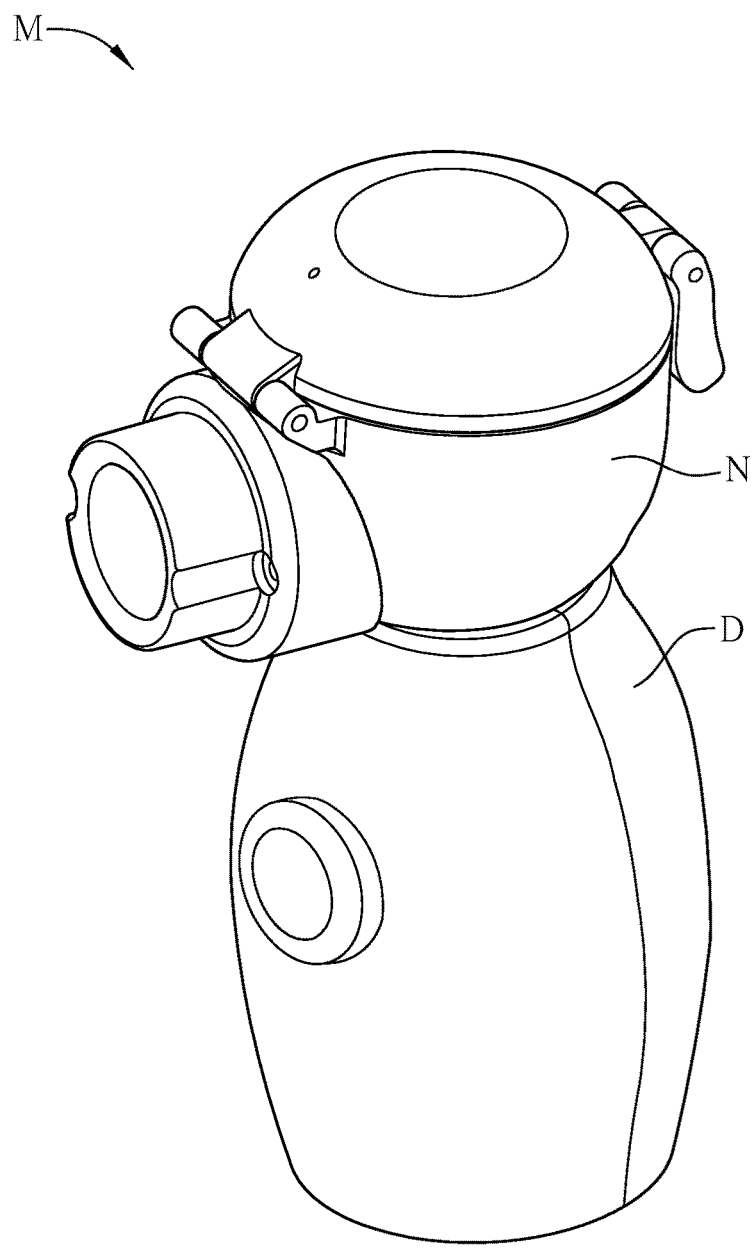
FIG. 5 is a schematic diagram of a nebulizer of an embodiment of the invention.

As shown in FIG. 5, a nebulizer M is further provided. The nebulizer M includes a nebulizing device N and a nebulization driving device D. Because the nebulizing device N has been clearly illustrated in the above embodiments, the illustration thereof is omitted here for conciseness. In this embodiment, the nebulization driving device D connects to and drives the nebulizing unit 2 of the nebulizing device N to spray the nebulized drops. The nebulization driving device D is detachably coupled with the storage module 1 of the nebulizing device N. The nebulization driving device D can contain a power unit to provide the required power for the operation of the nebulizing device N. Besides, the nebulization driving device D can contain a control board to control the operation of the nebulizing device N.

Summarily, in the nebulizing device and the nebulizer of this invention, the size of the second opening of the first waterproof gasket is greater than that of the first opening, so that the annular wall structure is extended from the first opening toward the second opening to form a non-horizontal surface. Therefore, even if the nebulized drops are condensed into water drops after being sprayed out of the nozzle plate, the water drops will flow to the outside of the second opening instead of becoming standing water at the annular wall structure. Therefore, the nebulizing unit will not be soaked in the standing water containing the medicament for a long time, and the nebulizing unit may be oxidized or eroded by the medicament as little as possible so the lifespan of the nebulizing unit can be extended.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A nebulizing device, comprising:

a storage module, comprising:

a bottom wall;

a tubular sidewall connected to the circumference of the bottom wall, wherein the tubular sidewall and the bottom wall form an accommodating recess having an upper opening to accommodate a liquid, the tubular sidewall comprises an outlet, and the bottom wall is extended to the outlet; and a coupling part connected to an outer surface of the tubular sidewall and aligned with the outlet, and comprising an extension wall and a first recess;

a nebulizing unit disposed within the first recess to transform the liquid outputted by the outlet into a plurality of nebulized drops; and a first waterproof gasket disposed within the first recess and located on a side of the nebulizing unit farther from the outlet, comprising:

a first opening disposed adjacent to the nebulizing unit;

a second opening disposed opposite to the first opening and away from the nebulizing unit, wherein the size of the second opening is greater than that of the first opening; and an annular wall structure connected to the first opening and the second opening.

2. The nebulizing device as recited in claim 1, wherein the annular wall structure is extended from the first opening toward the second opening to form a non-horizontal surface.

3. The nebulizing device as recited in claim 1, wherein the annular wall structure has a concave surface, a flat surface, a jagged surface or a ladder-shaped surface.

4. The nebulizing device as recited in claim 1, wherein the nebulizing unit comprises a piezoelectric element and a nozzle plate, the piezoelectric element is disposed around the nozzle plate, and the first waterproof gasket tightly abuts on the piezoelectric element.

5. The nebulizing device as recited in claim 4, further comprising a guiding tube detachably coupled with the coupling part of the storage module.

6. The nebulizing device as recited in claim 5, wherein the guiding tube comprises a connection portion, an opening and a tube portion, wherein the connection portion is coupled with the extension wall of the coupling part, the opening is correspondingly disposed at or aligned with the nozzle plate, and the guiding tube guides the plurality of nebulized drops sprayed out by the nebulizing unit.

7. The nebulizing device as recited in claim 5, wherein the coupling part further comprises an annular groove disposed on the extension wall of the coupling part and facing an end surface of the guiding tube.

8. The nebulizing device as recited in claim 7, further comprising a second waterproof gasket partially disposed within the annular groove and partially extended outwards to cover the end surface of the guiding tube.

9. The nebulizing device as recited in claim 8, wherein the second waterproof gasket prevents an external liquid from permeating into a region where an electrode is located through the gap between the guiding tube and the coupling part to avoid the short circuit of the electrode assembly.

10. The nebulizing device as recited in claim 1, further comprising a third waterproof gasket, wherein the third waterproof gasket and the first waterproof gasket form a hermetic space at one end of the first recess.

11. A nebulizer, comprising:

a nebulizing device, comprising:

a storage module, comprising:

a bottom wall;

a tubular sidewall connected to the circumference of the bottom wall, wherein the tubular sidewall and the bottom wall form an accommodating recess having an upper opening to accommodate a liquid, the tubular sidewall comprises an outlet, and the bottom wall is extended to the outlet; and a coupling part connected to an outer surface of the tubular sidewall and aligned with the outlet, and comprising an extension wall and a first recess;

a nebulizing unit disposed within the first recess to transform the liquid outputted by the outlet into a plurality of nebulized drops and spray them out; and a first waterproof gasket disposed within the first recess and located on a side of the nebulizing unit farther from the outlet, comprising:

a first opening disposed adjacent to the nebulizing unit;

a second opening disposed opposite to the first opening and located on a side of the first opening farther from the nebulizing unit, wherein the size of the second opening is greater than that of the first opening; and an annular wall structure connected to the first opening and the second opening; and a nebulization driving device connecting to and driving the nebulizing unit to spray the nebulized drops.

12. The nebulizer as recited in claim 11, wherein the annular wall structure is extended from the first opening toward the second opening to form a non-horizontal surface.

13. The nebulizer as recited in claim 11, wherein the annular wall structure has a concave surface, a flat surface, a jagged surface or a ladder-shaped surface.

14. The nebulizer as recited in claim 11, wherein the nebulizing unit comprises a piezoelectric element and a nozzle plate, the piezoelectric element is disposed around the nozzle plate, and the first waterproof gasket tightly abuts on the piezoelectric element.

15. The nebulizer as recited in claim 14, wherein the nebulizing device further comprises a guiding tube which is detachably coupled with the coupling part of the storage module.

16. The nebulizer as recited in claim 15, wherein the guiding tube comprises a connection portion, an opening and a tube portion, wherein the connection portion is coupled with the extension wall of the coupling part, the opening is correspondingly disposed at or aligned with the nozzle plate, and the guiding tube guides the plurality of nebulized drops sprayed out by the nebulizing unit.

17. The nebulizer as recited in claim 16, wherein the coupling part further comprises an annular groove which is disposed on the extension wall of the coupling part and faces an end surface of the guiding tube.

18. The nebulizer as recited in claim 17, wherein the nebulizing device further comprises a second waterproof gasket which is disposed within the annular groove and extended outwards to cover the end surface of the guiding tube.

19. The nebulizer as recited in claim 18, wherein the second waterproof gasket is extended along a sidewall of the terminal of the extension wall, and a section of the second waterproof gasket has a mushroom shape.

20. The nebulizer as recited in claim 11, wherein the nebulizing device further comprises a third waterproof gasket, wherein the third waterproof gasket and the first waterproof gasket form a hermetic space disposing with an electrode at one end of the first recess.

* * * * *